US007052855B2

(12) United States Patent
Uchida et al.

(10) Patent No.: US 7,052,855 B2
(45) Date of Patent: *May 30, 2006

(54) ANTI-APO-B-48 MONOCLONAL ANTIBODY, HYBRIDOMA PRODUCING THE SAME, AND METHOD FOR MEASURING APO-B-48 USING THE SAME

(75) Inventors: Yoshiaki Uchida, Chuo-ku (JP); Yoshihiro Kurano, Chuo-ku (JP)

(73) Assignee: Fujirebio, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/682,992

(22) Filed: Oct. 14, 2003

(65) Prior Publication Data

US 2004/0175755 A1 Sep. 9, 2004

Related U.S. Application Data

(63) Continuation of application No. 09/892,844, filed on Jun. 28, 2001, now abandoned, which is a continuation of application No. 09/172,661, filed on Oct. 15, 1998, now Pat. No. 6,309,844.

(30) Foreign Application Priority Data

Oct. 15, 1997  (JP)  .............................. 97-2994739

(51) Int. Cl.
   *G01N 33/53* (2006.01)
(52) U.S. Cl. ...................... 435/7.1; 435/7.9; 435/7.95; 435/960; 435/961; 435/971; 435/805; 436/13; 436/808; 530/387.1; 530/388.1; 530/389.3
(58) Field of Classification Search ................. 435/7.1, 435/7.9–7.95, 960, 961, 971; 436/514, 518; 530/388.1, 387.1, 389.3
See application file for complete search history.

(56) References Cited

U.S. PATENT DOCUMENTS 4,828,986 A     5/1989  Smith et al.
6,309,844 B1 * 10/2001  Uchida et al. ............... 435/7.1

OTHER PUBLICATIONS

Albers e al., Journal of Lipid Research. vol. 30, pp. 1445-1458, 1989.*
Peel et al., Clinical Science. vol. 85, pp. 521-524. 1993.*
Roitt, Ivan M. Essential Immunology. Blackwell Scientific Publications. pp. 107-110. 1988.*
European Search Report.
Patent Abstracts of Japan, vol. 010, No. 148, May 29, 1986 & JP 61007299 A, Jan. 13, 1986.
J. Albers et al: "Evaluation of a monoclonal antibody-based enzyme-linked immunosorbent assay as a candidate reference method for the measurement of apolipoprotein B-100," *Journal of Lipid Research*, vol. 30, No. 9, Sep. 1989, pp. 1445-1458.

M. Phillips et al: "A Single Copy Of Apolipoprotein B-48 is present on the human chylomicron remnant," *Journal of Lipid Research*, vol. 38, No. 6, Jun. 1997, pp. 1170-1177.
S. Fantappie et al; "Monoclonal antibodies to human low density lipoprotein identify distinct areas on apolipoprotein B-100 relevant to the low density lipoprotein-receptor interaction," *Journal of Lipid Research*, vol. 33, No. 8, Aug. 1992, pp. 1111-1121.
R. Pease et al: "Use of bacterial expression cloning to localize the epitopes for a series of monoclonal antibodies agianst apolipoprotein B100," *The Journal of Biological Chemistry*, vol. 265, No. 1, Jan. 5, 1990, pp. 553-568.
A. Corsini et al: "Monoclonal antibody 5A inhibits the LDL-receptor interaction, and recognizes Apo B-48," *Arteriosclerosis*, vol. 8, No. 5, Sep. 1998, pp. 635A-636A.
Tada et al: Clinical Test, vol. 40, No. 9/96 pp. 1023-1029.
Kinoshita et al: Program and Abstract of the 30th General Meeting of Japan Arterial Sclerosis Association held on Jun. 11-12, 1998 Nos. 160-0023 and 03-3344-0111.
Burdon et al, Laboratory Techiques in Biochemistry and molecular Biology. vol. 13, pp. 186-215; 1984.
Roitt, Ivan, Essentiall Immunology. Sixth Edition, pp. 107-110; 1988.
Y. Uchida et al: "Establishment of monoclonal antibody against human Apo B-48 and measurement of Apo B-48 in serum by ELISA method," *Journal of Clinical Laboratory Analysis*, vol. 12, No. 5, 1998, pp. 289-292.
Yang et al Nature vol. 323 Oct. 1986 pp 738-742 Sequence, structure receptor-binding domains and internal repeats of human apolipoprotein B-100.
Blackhart et al The J. of Biological Chemistry vol 265 No. 15, May 25, 1990 pp. 8358-8360 An Expression System for Human Apolipoprotein B100 in a Rat-Hepatoma Cell Line.
Yao et al The J. of Biological Chemistry vol. 267, No. 2 Jan. 15, 1992 pp. 1175-1182 Elimination of Apolipoprotein B48 Formation in Rat Hepatoma Cell Lines Transfected with Mutant Human Apolipoprotein B cDNA Constructs.
Peel et al Clinical Science (1993) 85 521-524 A Novel antiserum specific to apolipoprotein B-48 etc.
Rinsho Kensa, vol. 40 No. 9 1996 pp. 1023-1029.
Japanese article 30 1998 (on cover) Nos. 160-0023 and 03-3344-0111.
Young et al New England J. of Medicine Jun. 1989 pp. 1604-1610 Familial Hypobetalipoproteinemia etc.
Innerarity et al Rapid Publication pp. 1794-1798 Structural Relationship of Human Apolipoprotein B48 etc.

(Continued)

Primary Examiner—Bao-Thuy L. Nguyen
(74) Attorney, Agent, or Firm—Nixon & Vanderhye P.C.

(57) ABSTRACT

A novel monoclonal antibody which specifically binds to apo-B-48 is disclosed. The monoclonal antibody specifically binds to apo-B-48 but does not bind to apo-B-100.

3 Claims, 6 Drawing Sheets

OTHER PUBLICATIONS

Yao et al J. of Biological Chemistry vol. 266, No. 5, Feb. 15, 1991 pp 3300-3308 Expression of Carboxyl-terminally etc.

Uchida et al J. Clinical Laboratory Analysis 12:289-292 (1998) Establishment of Monoclonal Antibody etc.

Lovegrove et al Biochimica et Biophysica Acta 1301 (1996) 221-229 Quantitation of apolipoprotein B-48 etc.

Schneeman et al Proc. Natl. Acad. Sci US vol. 90, pp 2069-2073 Mar. 1993 Medicinal Sciences Relationships between the responses of triglyceride-rich lipoproteins etc.

Smith et al Ann Clin Biochem 1997 34 185-189 A highly sensitive assay for quantitation etc.

* cited by examiner

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: synthetic
      peptide derived from Apo-B-48

<400> SEQUENCE: 1

Cys Thr Tyr Met Ile
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: synthetic
      peptide derived from Apo-B-48

<400> SEQUENCE: 2

Cys Gln Thr Tyr Met Ile
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: synthetic
      peptide derived from Apo-B-48

<400> SEQUENCE: 3

Cys Leu Gln Thr Tyr Met Ile
 1               5

ANTI-APO-B-48 MONOCLONAL ANTIBODY, HYBRIDOMA PRODUCING THE SAME, AND METHOD FOR MEASURING APO-B-48 USING THE SAME

The present application is a continuation of application Ser. No. 09/892,844, filed Jun. 28, 2001, now abandoned, which is a continuation of application Ser. No. 09/172,661, filed Oct. 15, 1998 (now U.S. Pat. No. 6,309,844), the entire contents of each of which is hereby incorporated by reference.

BACKGROUND OF THE INVENTION

I. Field of the Invention

The present invention relates to a monoclonal antibody which specifically binds to apo-B-48, hybridoma producing the same and method for measuring apo-B-48 using the monoclonal antibody. The monoclonal antibody is useful for diagnosis and therapy of hyperlipidemia and arterial sclerosis.

II. Description of the Related Art

Arterial sclerosis is one of the typical adult diseases and establishment of effective diagnosis and therapy of this disease is longed for. The causes of arterial sclerosis include increase in the amounts of various lipoproteins contained in the blood circulating the body, which accelerate deposition of cholesterol on the inner walls of blood vessels, and decrease in various lipoproteins which prevent such deposition of cholesterol.

Representative lipoproteins which are known to participate in hyperlipidemia include chylomicron (CM), chylomicron remnant (CM remnant) which is an intermediate metabolite of CM in the blood, very low density lipoprotein (VLDL), very low density lipoprotein remnant (VLDL remnant) which is an intermediate metabolite of VLDL in the blood, low density lipoprotein (LDL) and high density lipoprotein (HDL).

CM remnant, VLDL remnant and the like are called remnant-like particles (RLP). The remnant-like particles as well as LDL are lipoproteins which transport cholesterol to the blood vessel walls. Therefore, to decrease the blood levels of these lipoproteins is a direct therapy of arterial sclerosis. On the other hand, since HDL, for example, has a function to withdraw cholesterol from the lesion of arterial sclerosis, to increase the blood level of HDL is useful for the therapy of arterial sclerosis.

Among the above-mentioned lipoproteins, RLP has been reported to participate in expression of arterial sclerosis due to postprandial hyperlipidemia, and is now thought as an important risk factor of arterial sclerosis. Known apolipoproteins constituting RLP include apo-C, apo-E, apo-A-I, apo-B-100 and apo-B-48.

One of the known methods for measuring blood level of RLP is the RLP-C (remnant-like particles cholesterol) method. In the RLP-C method, anti-apo-A-I monoclonal antibody and anti-apo-B-100 monoclonal antibody are immobilized on a gel, and the gel is reacted with a test sample, followed by removal of the lipoproteins bound to these antibodies by centrifugation. Thereafter, the amount of the lipoprotein remaining in the supernatant is measured in terms of the amount of cholesterol.

Apo-A-I occurs as a major apolipoprotein of CM and HDL, and apo-B-100 occurs as a major apolipoprotein of VLDL, VLDL remnant and LDL.

Thus, theoretically, CM and HDL are bound to the anti-apo-A-I monoclonal antibody, and VLDL, VLDL remnant and LDL are bound to anti-apo-B-100 monoclonal antibody. Thus, in the RLP-C method, these lipoproteins are removed.

The anti-apo-B-100 monoclonal antibody specifically recognizes the region of the 2291st to 2318th amino acids, so that it does not recognize apo-B-48 which consists of the 1st to 2152nd amino acids of apo-B-100. Therefore, the lipoprotein which contains apo-B-48 as an apolipoprotein but does not contain apo-B-100 as an apolipoprotein is measured by the RLP-C method.

The structure of the epitopes on the apolipoproteins and the homigenity of the epitopes in the plasma lipoprotein population still remain unclear.

In the RLP-C method, the above-mentioned removal of the various lipoproteins by binding the lipoproteins to the gel is indispensable. However, this step is troublesome and has poor reproducibility because the degree of removal varies from run to run. Therefore, the measured values are not very reliable.

Apo-B-48 is contained as an apolipoprotein in CM and CM remnant. CM is quickly converted to CM remnant after eating by lipoprotein lipase and the CM remnant is taken into the liver through remnant receptors existing in the liver, so that CM does not exist in the blood when fasted. That is, Chylomicrons are lipoproteins synthesized exclusively by the intestine to transport dietary fat and fat-soluble vitamins. Among the apoliporotenis found in chylomicrons, such as apo-B-48, apo-A-I, apo-A-IV and Cs, only the synthesis of apo-B-48 is required for the assembly of chylomicrons. Apo-B-48 is a 2152 amino acid long polypeptide translated and pooled in the adult intestine from the same gene as apo-B-100 by the action of a series of enzymes. During circulation in the blood, chylomicrons are exposed to lipolysis and apolipoprotein exchange, and are converted into "chylomicron remnants". Therefore, if there is a monoclonal antibody which specifically recognizes apo-B-48, CM remnant alone can be directly measured by using the blood when fasted as a test sample as a risk marker for postprandial lipidemia and/or arterial sclerosis. This makes it possible to accurately diagnose hyperlipidemia and, in turn, is useful for diagnosis and therapy of arterial sclerosis.

Apo-B-48 has the same amino acid sequence as a part of the amino acid sequence of apo-B-100. The amino acid sequences of both apo-B-100 and apo-B-48 are known (Nature, Vol. 323, p.738, October, 1986). An anti-apo-B-48 antiserum is also known (Journal of Biological Chemistry, Vol. 265, No. 15, p.8358, 1990; Journal of Biological Chemistry, Vol. 267, No. 2, p.1176, 1992; and Clinical Science, Vol. 85, p.521, 1993).

However, a monoclonal antibody which specifically binds to apo-B-48 alone has not been reported. Moreover, a reference (RINSHO KENSA, Vol. 40, No. 9 (1996), p. 1025, left column, line 8 from the bottom) describes that it is theoretically difficult to produce an antibody which specifically reacts with apo-B-48 alone.

SUMMARY OF THE INVENTION

Accordingly, an object of the present invention is to provide a monoclonal antibody which specifically reacts with apo-B-48 alone. Another object of the present invention is to provide a hybridoma which produces the monoclonal antibody according to the present invention. Still another object of the present invention is to provide a method for measuring apo-B-48 in a test sample using the monoclonal antibody according to the present invention. Still another object of the present invention is to provide a reagent and a kit for immunoassay for measuring apo-B-48 in a test sample.

The present inventors intensively studied to provide a monoclonal antibody which specifically reacts with apo-B-48 alone, to succeed in obtaining such a monoclonal antibody by using a conjugate of a very small peptide consisting of the C-terminal region of apo-B-48 and a carrier protein as an immunogen.

That is, the present invention provides a monoclonal antibody which specifically binds to apo-B-48 and which does not specifically bind to apo-B-100. The present invention also provides a hybridoma which produces the monoclonal antibody according to the present invention. The present invention further provides a method for measuring apo-B-48 in a test sample, comprising utilizing antigen-antibody reaction between apo-B-48 in the test sample and the monoclonal antibody according to the present invention. The present invention still further provides a reagent for immunoassay for measuring apo-B-48 comprising the monoclonal antibody according to the present invention. The present invention still further provides a kit for immunoassay for measuring apo-B-48 comprising the monoclonal antibody according to the present invention.

By the present invention, a monoclonal antibody which specifically binds to apo-B-48 and which does not specifically bind to apo-B-100 was first provided. Since the monoclonal antibody according to the present invention specifically binds to apo-B-48 but does not specifically bind to apo-B-100, apo-B-48 alone can be measured. Thus, the monoclonal antibody of the present invention is useful for the diagnosis and therapy of arterial sclerosis.

DETAILED DESCRIPTION OF THE PREFERRED EMBODIMENTS

Figure 1:
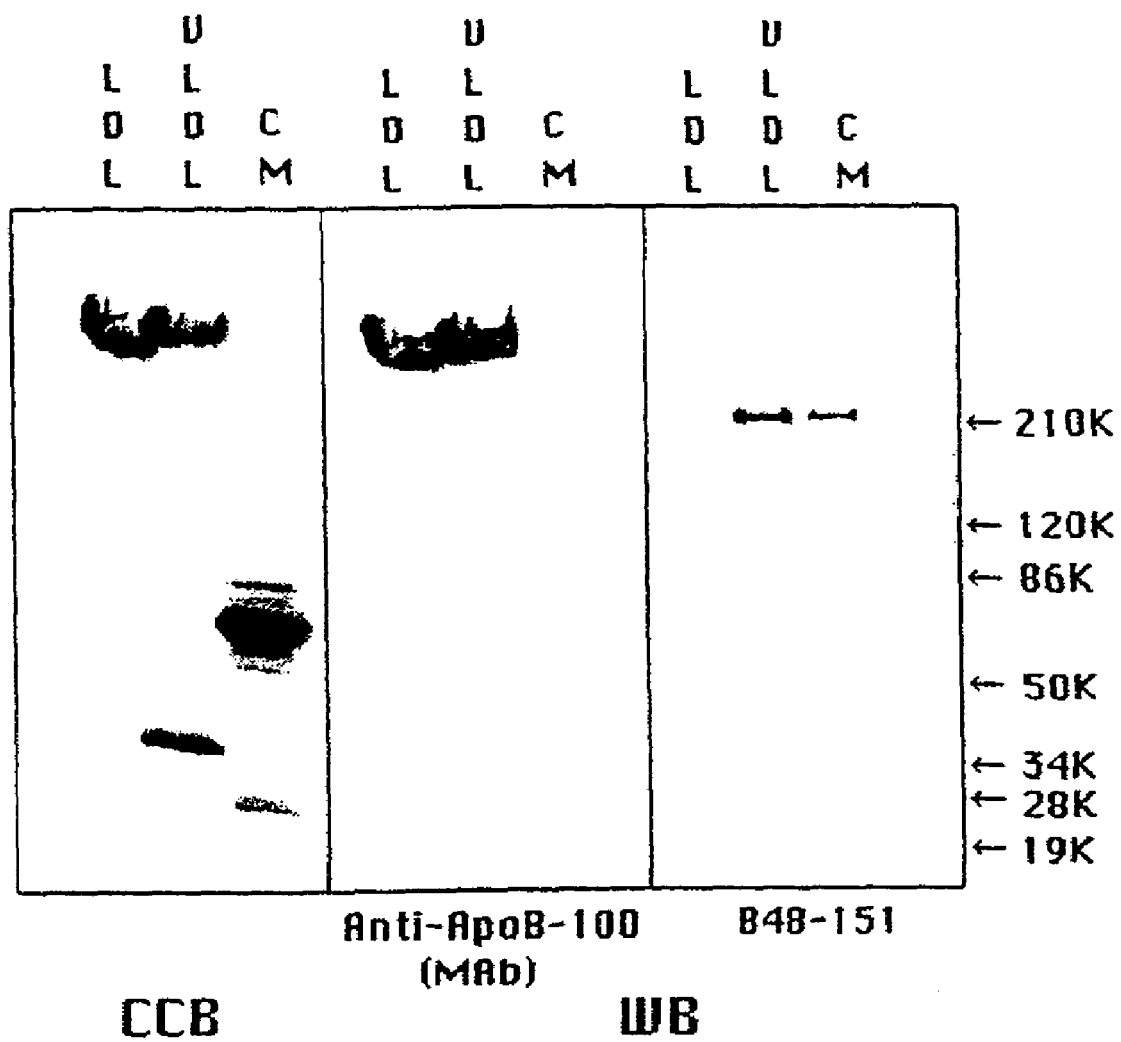
FIG. 1 schematically shows the results of the Western blot showing the reactions between monoclonal antibody B48-151 of the present invention and various lipoprotein fractions, which results were obtained in Example 5.

As mentioned above, the monoclonal antibody according to the present invention specifically binds to apo-B-48 and does not specifically bind to apo-B-100. The corresponding epitope of the monoclonal antibody according to the present invention may preferably reside in the C-terminal region of apo-B-48. The C-terminal region may preferably be 1st to 20th, more preferably 1st to 10th amino acids from the C-terminal of apo-B-48. The corresponding epitope may preferably include the C-terminal of apo-B-48. As will be described later in detail, the corresponding epitope of the preferred monoclonal antibody actually produced in the examples is the peptide consisting of only 6 amino acids of the C-terminal region of apo-B-48.

The monoclonal antibody according to the present invention may be obtained as follows:

First, a peptide derived from apo-B-48 is synthesized. The peptide may preferably consists essentially of 5 to 20 amino acids, more preferably 5 to 10 amino acids from the C-terminal of apo-B-48 (excluding cystein which may be attached to the N-terminal of the peptide). For example, a peptide consisting of the 6 amino acids from the C-terminal of apo-B-48, to which cystein is attached at the N-terminal thereof, that is, a peptide consisting of 7 amino acids having the sequence of Cys Leu Gln Thr Tyr Met Ile (this peptide is hereinafter referred to as "C6") is synthesized.

The peptide derived from apo-B-48, such as the above-mentioned C6, is then conjugated with a carrier protein such as hemocyanin. The C6 may be bound to the carrier protein through the N-terminal cystein. This may be accomplished by the method described in detail in the Examples below.

Using the thus obtained conjugate as the immunogen, the monoclonal antibody according to the present invention may be prepared by the well-known conventional method. An example of the method is described in detail in the Examples below. Briefly, a mammal is immunized with the conjugate and antibody-producing cells, such as lymphocytes and spleen cells are collected from the immunized mammal. The antibody-producing cells are then fused with myeloma cells, and hybridomas are selected by selective culture. The monoclonal antibodies produced by the obtained hybridomas are then tested for their specificities by Western blot (WB) method or by ELISA using apo-B-48 or apo-B-100 as an antigen, and the hybridomas producing monoclonal antibodies which bind to apo-B-48 and do not bind to apo-B-100 are selected, thereby obtaining the monoclonal antibody according to the present invention. As the antigen, not only the free apolipoproteins, but also lipoproteins containing the apolipoproteins may be employed.

By this method which is described in more detail in the Examples below, a hybridoma named B48-151 producing the monoclonal antibody according to the present invention was obtained. The hybridoma B48-151 has been deposited according to the Budapest Treaty with National Institute of Bioscience and Human-Technology, Agency of Industrial Science and Technology at 1-3, Higashi 1-chome, Tsukuba-shi, Ibaraki 305-0046 Japan under accession No. FERM BP-6473.

The monoclonal antibody produced by the hybridoma B48-151 is a preferred monoclonal antibody according to the present invention, which strongly and specifically reacts with apo-B-48 and do not specifically react with apo-B-100 at all. Monoclonal antibodies produced by variants of the hybridoma B48-151 are also preferred. The term "variant" herein means the hybridomas derived from the hybridoma B48-151 having the same or modified physiological and/or morphological characters as the hybridoma B48-151 and produces a monoclonal antibody which specifically binds to apo-B-48 and which does not specifically bind to apo-B-100.

The monoclonal antibody according to the present invention may be used for measuring apo-B-48 in a test sample by immunoassay. Since not only free apo-B-48, but also apo- B-48 contained in lipoproteins can be measured, the monoclonal antibody may be used for immunoassays for measuring the lipoproteins containing apo-B-48.

In the present specification and claims, the term "measure" includes both quantification and detection.

The test sample may be a body fluid such as blood, serum or blood plasma, as well as dilutions thereof, although the test sample is not restricted thereto.

Various methods for immunoassay are well-known in the art and the monoclonal antibody according to the present invention may be applied to any of these methods. That is, known immunoassay methods include, when classified according to the reaction mode, sandwich methods, immunoblotting methods, competition methods, agglutination methods and so on. When classified according to the label used, known immunoassays include enzyme immunoassays, radio immunoassays, fluorescence immunoassays, biotin immunoassays and so on.

Among these, sandwich ELISA and Western blot are preferred. These methods per se are well-known in the art, and detailed methods are described in the Examples below.

Briefly, sandwich ELISA may be carried out, for example, as follows. That is, the monoclonal antibody of the present invention is immobilized on a solid carrier such as walls of wells in a microtiter plate or microbeads. After the immobilization, the solid carrier is blocked with proteins such as skim milk, casein, gelatin, bovine serum albumin or the like to prevent non-specific binding of the antigen. A test sample is applied to the solid carrier and antigen-antibody reaction is allowed to occur. After washing the carrier, an enzyme-labeled second antibody to apo-B-48 is applied and antigen-antibody reaction is allowed to occur. After washing, the second antibody bound to the carrier is measured based on the color reaction after adding a substrate of the enzyme.

Western blot method may be carried out, for example, as follows. That is, a test sample is subjected to fractionation by gel electrophoresis such as SDS-PAGE, and the electrophoretic pattern is transferred onto a membrane such as nitrocellulose membrane. After blocking the membrane, the monoclonal antibody of the present invention is applied to the membrane and antigen-antibody reaction is allowed to occur. After washing, a labeled second antibody to the monoclonal antibody is applied and antigen-antibody reaction is allowed to occur. After washing, the second antibody bound to the membrane is measured by measuring the label.

In the method of the present invention, it is preferred to subject the test sample to a treatment which exposes the epitope of apo-B-48, which epitope is recognized by the monoclonal antibody according to the present invention. That is, in cases where the monoclonal antibody according to the present invention recognizes the C-terminal region of apo-B-48, and where the test sample is a body fluid containing lipoprotein particles or a dilution thereof, the antigen-antibody reaction between apo-B-48 and the monoclonal antibody may not occur very well because the C-terminal region of apo-B-48 may not be well exposed in lipoprotein particles. Thus, in such a case, it is preferred to expose the C-terminal region of apo-B-48.

Exposing the C-terminal region of apo-B-48 may be accomplished by treating the test sample with a surfactant, or by subjecting the test sample to freeze-thaw cycle at least once.

As the surfactant useful for exposing the C-terminal region of apo-B-48, nonionic surfactants including polyoxyethylene-p-t-octylphenyl ethers such as Triton X-100 (trademark), Triton X-114 (trademark) and Nonidet P-40 (trademark); and polyoxyethylerie sorbitane alkyl esters such as Tween 20 (trademark). These surfactants may be employed individually or in combination. In cases where a Triton series surfactant such as Triton X-114 (trademark) which has high epitope-exposing ability but not dissolved well at room temperature is employed, it is preferred to use a mixture of the Triton series surfactant and a Tween series surfactant such as Tween 20 (trademark) which is well dissolved at room temperature and which does not substantially inhibit the antigen-antibody reactions.

Although use of SDS to expose an epitope of apo-B-48 has been reported (Makoto KINOSHITA et al., Abstract of the 30th Meeting of Japan Arterial Sclerosis Association held on Jun. 11 and 12, 1998, p.133), SDS is not preferred in the present invention because the antigen-antibody reaction may be inhibited.

Since surfactants tend to inhibit immunological reactions, the concentration of the surfactant may preferably be selected such that the surfactant does not substantially inhibit the immunological reactions. The preferred concentration of the surfactants may preferably be 0.01 to 2% by weight, more preferably 0.02 to 0.5% by weight. The treatment may preferably be carried out at 4 to 40° C. for 5 minutes to 48 hours in a buffer used for the antibody-antigen reaction. The surfactant may exist in the reaction mixture of the antigen-antibody reaction. Thus, the treatment may be carried out simultaneously with the antigen-antibody reaction, or before the antigen-antibody reaction.

The epitope of apo-B-48 may also be exposed with destroying the structure of the lipoproteins by repeating freezing and thawing cycle of the test sample. The freeze-thaw cycle may be carried out at least once.

The present invention also provides a key reagent for immunoassay for measuring apo-B-48. The reagent may be in the form of a solid carrier on which the monoclonal antibody of the present invention is immobilized. The monoclonal antibody may be immobilized on gelatin particles or latex particles by a conventional method to prepare a reagent for immunoassay by agglutination method. Similarly, the monoclonal antibody may be immobilized on a solid carrier such as walls of wells of microtiter plate, polymers such as polystyrene, glass beads, magnetic particles, filter paper for immunochromatography, glass filter or the like by a conventional method to prepare reagent for enzyme immunoassay (EIA), ELISA, radio immunoassay (RIA) or the like.

Further, the present invention also provide a kit for immunoassay for measuring apo-B-48. The kit may comprise, in addition to the above-mentioned reagent including the monoclonal antibody of the present invention bound to a solid carrier, at least one or more of a second labeled antibody, reagents for measuring the label of the second antibody, blocking agent, buffer and the like.

EXAMPLES

The present invention will now be described by way of examples thereof. The Examples are presented for the illustration purpose only and should not be interpreted in any restrictive way.

Example1

Synthesis of Peptide Originated from Apo-B-48

A peptide consisting of the 4 amino acids from the C-terminal of apo-B-48, to which cystein was attached at the N-terminal thereof, that is, a peptide consisting of 5 amino acids having the sequence of Cys Thr Tyr Met Ile (this peptide is hereinafter referred to as "C4") was synthesized by a commercially available peptide synthesizer.

Similarly, a peptide consisting of the 5 amino acids from the C-terminal of apo-B-48, to which cystein was attached at the N-terminal thereof, that is, a peptide consisting of 6 amino acids having the sequence of Cys Gln Thr Tyr Met Ile (this peptide is hereinafter referred to as "C5") was synthesized.

Similarly, a peptide consisting of the 6 amino acids from the C-terminal of apo-B-48, to which cystein was attached at the N-terminal thereof, that is, a peptide consisting of 7 amino acids having the sequence of Cys Leu Gln Thr Tyr Met Ile (this peptide is referred to as "C6" as mentioned above) was synthesized.

The synthesis of the peptides was carried out using an automatic peptide synthesizer PSSM-8 commercially available from Shimazu Corporation, Kyoto, Japan, for simultaneous synthesis of a plurality of species by solid method. All of the amino acids were L-amino acids. The α-amino group was protected by 9-fluorenylmethoxycarbonyl group (Fmoc group), the β-sulfhydryl group of cystein and γ-carboxamide group of glutamine were protected by trityl group, and β-hydroxyl group of threonine and phenolic hydroxyl group of tyrosine were protected by t-butyl group.

As the solid carrier for initiating the peptide synthesis, 30 mg of HMP isoleucine resin (commercially available from Perkin Elmer) to which isoleucine (the C-terminal of the peptides) had been preliminarily attached in an amount of 0.65 mmol/g was used. For the condensation, 2-(1H-benzotriazole-1-yl)-1,1,3,3-tetramethyluroniumhexafluorophosphate, 1-hydroxybenzotriazole and N,N-diisopropylethylamine were used. For the removal of Fmoc group, 30% piperidine/DMF (dimethylformamide) solvent was used. As the solvent for reaction, DMF was used. The three peptides were simultaneously synthesized in accordance with the standard protocol described in the instructions attached to PSSM-8.

After the synthesis, the carriers to which the peptides containing the protective groups were attached were washed with methylene chloride and dried. The yields of C4, C5 and C6 were 41.0 mg, 48.4 mg and 52.6 mg, respectively.

Each of the carriers to which the peptide was bound was treated with trifluoroacetic acid solution (1 ml of trifluoroacetic acid, 50 μl of water, 75 mg of phenol, 50 μl of thioanisole and 50 μl of ethanediol) for 2 hours at room temperature to obtain free peptide chain. The peptide was precipitated with diethyl ether, and the precipitate was recovered by filtration. The precipitate was dissolved in water and freeze-dried. The yields of the thus obtained crude peptides C4, C5 and C6 were 12.23 mg, 16.17 mg and 17.04 mg, respectively.

The thus obtained crude peptides were purified by reverse phase high performance liquid chromatography. The column was Cosmosil 5C18-AR-300 (20 mm I.D.×150 mm L, commercially available from Nacalai Tesque) and elution was carried out with 18–28% linear gradient of aqueous acetonitrile solution containing 0.1% trifluoroacetic acid. The yields of the purified peptides C4, C5 and C6 after freeze-dry were 7.12 mg, 11.75 mg and 10.71 mg, respectively. Aliquots of these peptides were sampled and their sequences were confirmed by a protein sequencer (Procise 494 commercially available from Perkin Elmer).

Example 2

Synthesis of Peptide-KLH Conjugates

In 400 μl of 0.1 M phosphate buffer (pH 7.5), 5 mg of keyhole limpet hemocyanin (KLH) (commercially available from Calbiochem) was dissolved, and 1 mg of GMBS (N-γ-maleimidobutyryloxysuccinimide ester, commercially available from Dojindo Laboratories) was added to the solution, followed by stirring the resulting mixture at room temperature for 1 hour. The reaction mixture was applied to PD-10 column (commercially available from Pharmacia) equilibrated with 0.1 M phosphate buffer (pH 7.0) containing 1 mM of EDTA and eluted with the same buffer. The initial 2.5 ml was discarded and the subsequent 2.0 ml was collected.

To the resultant, about 1 mg of C4 synthesized in Example 1 in 1 ml of water was added and the mixture was stirred at room temperature for 2 hours. The reaction mixture was transferred to a dialysis tube and dialyzed against phosphate buffer (PBS) overnight. The same procedure was followed for C5 and C6 to obtain about 5 ml of solution of KLH-peptide conjugate for each peptide. The measured amounts of proteins for C4-KLH, C5-KLH and C6-KLH were 768 μg/ml, 861 μg/ml and 1140 μg/ml, respectively.

Example 3

Preparation of Lipoproteins from Human Serum

On 4 ml of pooled human serum collected 2 hours after eating, 4 ml of a solution prepared by dissolving 1.21 g of tris-hydroxymethyl aminomethane, 9.0 g of sodium chloride and 0.372 g of disodium EDTA in 1 liter of distilled water and then adjusting the pH to 7.4 (this solution is hereinafter referred to as "d=1.006 solution") was overlaid and the resultant was centrifuged at 26,000×g for 1 hour by Beckman ultracentrifuge. The upper layer was pooled as CM fraction. On the lower layer, the d=1.006 solution was overlaid and centrifuged at 114,000×g for 20 hours. The upper layer was pooled as VLDL fraction. The density of the lower layer was adjusted to 1.063 with sodium bromide solution and the resultant was centrifuged at 114,000×g for 20 hours. The supernatant was pooled as LDL fraction. The pooled fractions were concentrated and used as the antigens for the antigen-antibody reactions.

Example 4

Establishment of Hybridomas Producing

Anti-Apo-B-48 Monoclonal Antibody and Preparation of Anti-Apo-B-48 Monoclonal Antibody Hybridomas producing anti-apo-B-48 monoclonal antibodies were established by immunizing BALB/C mice with C4-KLH, C5-KLH or C6-KLH and fusing spleen lymphocytes recovered from the immunized mice and myeloma cells.

More particularly, C4-KLH, C5-KLH or C6-KLH were emulsified with Freund's complete adjuvant and the mice were immunized with the emulsions at a dose of 25 to 100 μg of the conjugate per mouse. Two to three weeks later, each of the conjugates was emulsified with Freund's incomplete adjuvant and the mice was additionally immunized with the emulsions at a dose of 25 to 100 μg of the conjugate per mouse. Sera from the mice were sampled and checked for the existence of anti-apo-B-48 antibody by Western blot (WB) method. The WB method was carried out in the same manner as the WB method described below, which was carried out for the screening of the desired monoclonal antibody. The mouse immunized with C6-KLH exhibited the strongest band in the WB method. To this mouse, 25 to 100 μg of free C6-KLH was administered intravenously. Three or four days after, spleen was removed from the mouse and spleen cells were prepared therefrom.

Mouse myeloma cells (P3U1) preliminarily cultured on RPMI-1640 medium and the obtained spleen cells were mixed at a ratio of 1:2 to 1:5, and cell fusion was carried out using PEG (purchased from Boehringer). The fused cells were suspended in HAT medium and then transferred to wells of a 96-well culture plate, followed by culturing the cells in a $CO_2$ incubator at 37° C.

The culture supernatants of the cells were screened by WB method. That is, the VLDL fraction prepared in Example 3 was subjected to 3–15% gradient SDS polyacrylamide gel electrophoresis (SDS-PAGE) and the electrophoretic pattern was transferred to a nitrocellulose membrane to prepare a blotting membrane. The blotting membrane was blocked with skim milk and then slit into the form of tapes. Each of the membranes in the form of a tape was inserted into each of the grooves of Accutran Incubation Tray (commercially available from S & S), and a mixture of pooled culture media from 6 wells of the 96-well culture plate was added to one of the grooves, followed by allowing reaction at room temperature for 1 hour under stirring.

The blotting membranes were washed three times with PBS containing 0.05% Tween 20 (trademark) (this buffer is hereinafter referred to as "washing buffer") for 5 minutes/wash under stirring, and peroxidase (POD)-labeled anti-mouse immunoglobulin antibody (purchased from Daco) was added to each groove, followed by allowing reaction at room temperature for 1 hour. The membranes were then washed with the washing buffer 4 times in the same manner as described above, and the substrate 4-chloronaphthol was added. Thereafter, existence of the bands corresponding to apo-B-48 was checked.

Using each of the culture media which constituted the mixture of the culture media from 6 wells added to the groove that expressed a positive band, WB was performed again as described above and the well producing the desired antibody was selected. The cells in the well were cloned by limiting dilution method. The cells producing the anti-apo-B-48 antibody were intraperitoneally administered to a mouse in a large amount, and ascites containing the anti-apo-B-48 monoclonal antibody was recovered from the mouse. The monoclonal antibody was purified from the ascites by using protein A-Sepharose (trademark).

This anti-apo-B-48 monoclonal antibody was named monoclonal antibody B48-151, and the hybridoma producing this monoclonal antibody B48-151 was named hybridoma B48-151.

Example 5

Confirmation of Reaction Specificity of Monoclonal Antibody B48-151

The reaction specificity of monoclonal antibody B48-151 was examined by WB method using CM, VLDL and LDL fractions.

More particularly, each of the above-mentioned fractions prepared in Example 3 as an antigen was subjected to 3–15% gradient SDS-PAGE and the obtained electrophoretic pattern was transferred to a nitrocellulose membrane. The obtained blotting membrane was blocked with skim milk and the resulting membrane was subjected to reaction with the antibodies. As the antibodies, the monoclonal antibody B48-151, and as controls, an anti-apo-B-100 monoclonal antibody MAB014 (purchased from Chemicon) and an anti-apo-B goat serum (purchased from Chemicon) were used. For further confirming the reaction specificity, inhibition test was carried out using free C6. Some of the blotting membranes were subjected to CCB staining to locate the positions of the proteins.

The antibody-antigen reactions were carried out as follows. Each of the antibodies was dissolved in phosphate buffer containing 1% bovine serum albumin (1% BSA-PBS) (pH7.4) to a concentration of 1 μg/ml and the resulting solution was allowed to react with each of the antigens blotted on the WB membrane at room temperature for 1 hour under stirring. After washing the membrane three times for five minutes per wash with the washing buffer, POD-labeled anti-mouse immunoglobulin antibody (purchased from Daco) was added to the membrane and the resultant was allowed to react at room temperature for 1 hour. After washing the membrane four times in the same manner as described above, a solution of the substrate 4-chloronaphthol was added, and the bands were observed. The results are shown in FIG. 1.

The inhibition test was carried out in the same manner as described above except that C6 was present at a concentration of 5 μg/ml in the reaction between the WB membrane and each of the antibodies. The results are shown in FIG. 2.

As shown in FIG. 1, use of the monoclonal antibody B48-151 exhibited a band only at the position corresponding to apo-B-48 having a molecular weight of a little more than 200,000, and a band corresponding to apo-B-100 having a molecular weight of about 550,000 was not observed.

Figure 2:
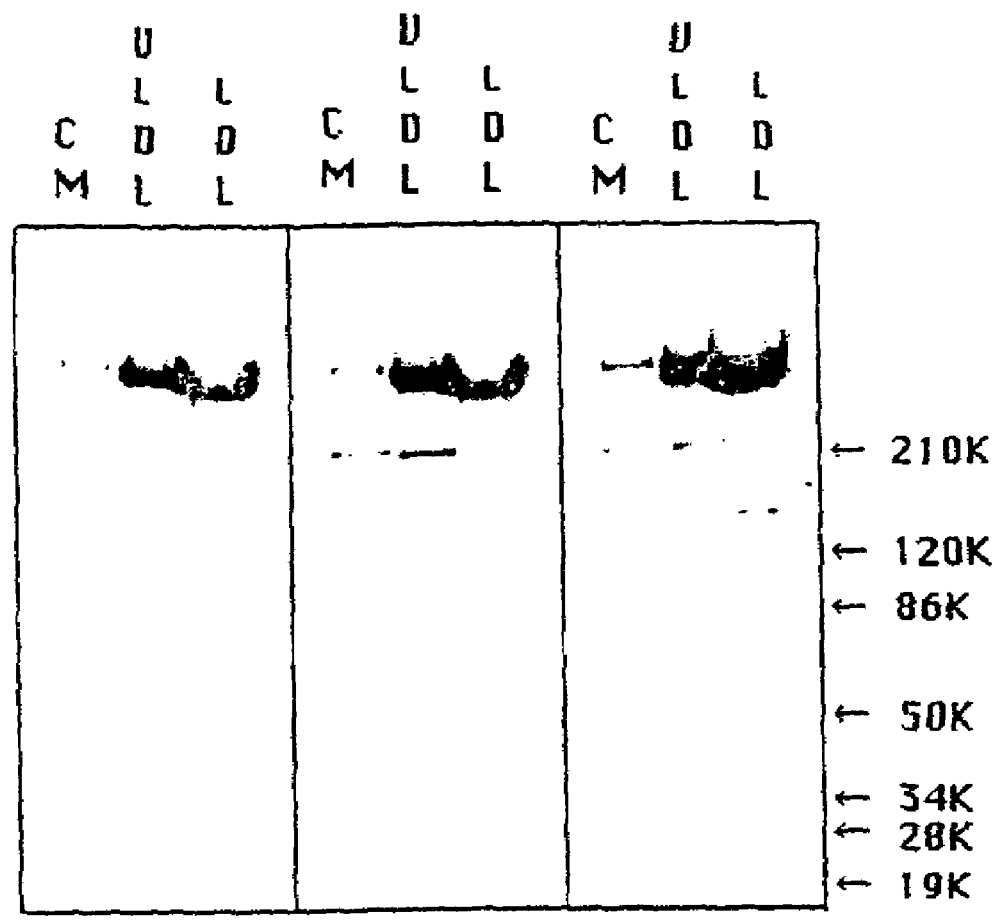
FIG. 2 schematically shows the results of the Western blot showing the reactions between monoclonal antibody B48-151 of the present invention and various lipoprotein fractions, when the reactions were inhibited by peptide C6, which results were obtained in Example 5.

As shown in FIG. 2, the band corresponding to apo-B-48 exhibited when the monoclonal antibody B48-151 was used disappeared under the coexistence of C6.

These results clearly indicate that the monoclonal antibody B48-151 specifically recognizes apo-B-48 but does not specifically recognize apo-B-100.

The band corresponding to apo-B-48 exhibited when VLDL fraction was used was the thickest is presumably because CM remnant is contained in the VLDL fraction. That is, since the fractions showing differences in particle size and weight were separated, the VLDL fractions may have been contaminated with chylomicron remnants to show immunoreactivity against apo-B-48.

Example 6

Measurement of Apo-B-48 by ELISA Using Immobilized Monoclonal Antibody B48-151

Sandwich ELISA was performed using the apo-B-48 as an antigen extracted from the SDS-PAGE gel.

More particularly, by the same method as described in Example 2, SDS-PAGE was performed. The portion of the gel containing the apo-B-48 band exhibited by using the VLDL fraction was cut out and the antigen was eluted from the gel by Electroeluter (commercially available from Bio Rad). On the other hand, to each of the wells of an ELISA plate (Maxisorb commercially available from Nunc), 75 μl of the monoclonal antibody B48-151 in PBS (pH7.4) at a concentration of 10 μg/ml was added and the plate was left to stand at 40° C. overnight, thereby adsorbing the antibody to the wells. To each well, 150 μl of 1% BSA-PBS (pH7.4) was placed and the plate was incubated at 37° C. for 5 hours, thereby carrying out masking. After washing the plate three times with the washing buffer, serially two-fold (2″) diluted purified apo-B-48 in 1% BSA-PBS from the concentration of 5 μg/ml was placed in each well in an amount of 75 μl/well and the resultant was allowed to react at 37° C. for 1 hour.

After washing the plate three times with the washing buffer, POD-labeled anti-human apo-B antibody (purchased from Chemicon) was placed in an amount of 75 µl/well, and the resultant was allowed to react at 37° C. for 1 hour.

The plate was then well washed with the washing buffer and the substrate ABTS was added to the wells in an amount of 75 µl/well and the resultant was left to stand at room temperature for 15 minutes, followed by measurement of absorbance at 405 nm.

To confirm reaction specificity, as a control, apo-B-100 (purchased from Chemicon) was serially diluted in the same manner as described above but from the concentration of 40 µg/ml, and used as antigens in the ELISA as described above.

Figure 3:
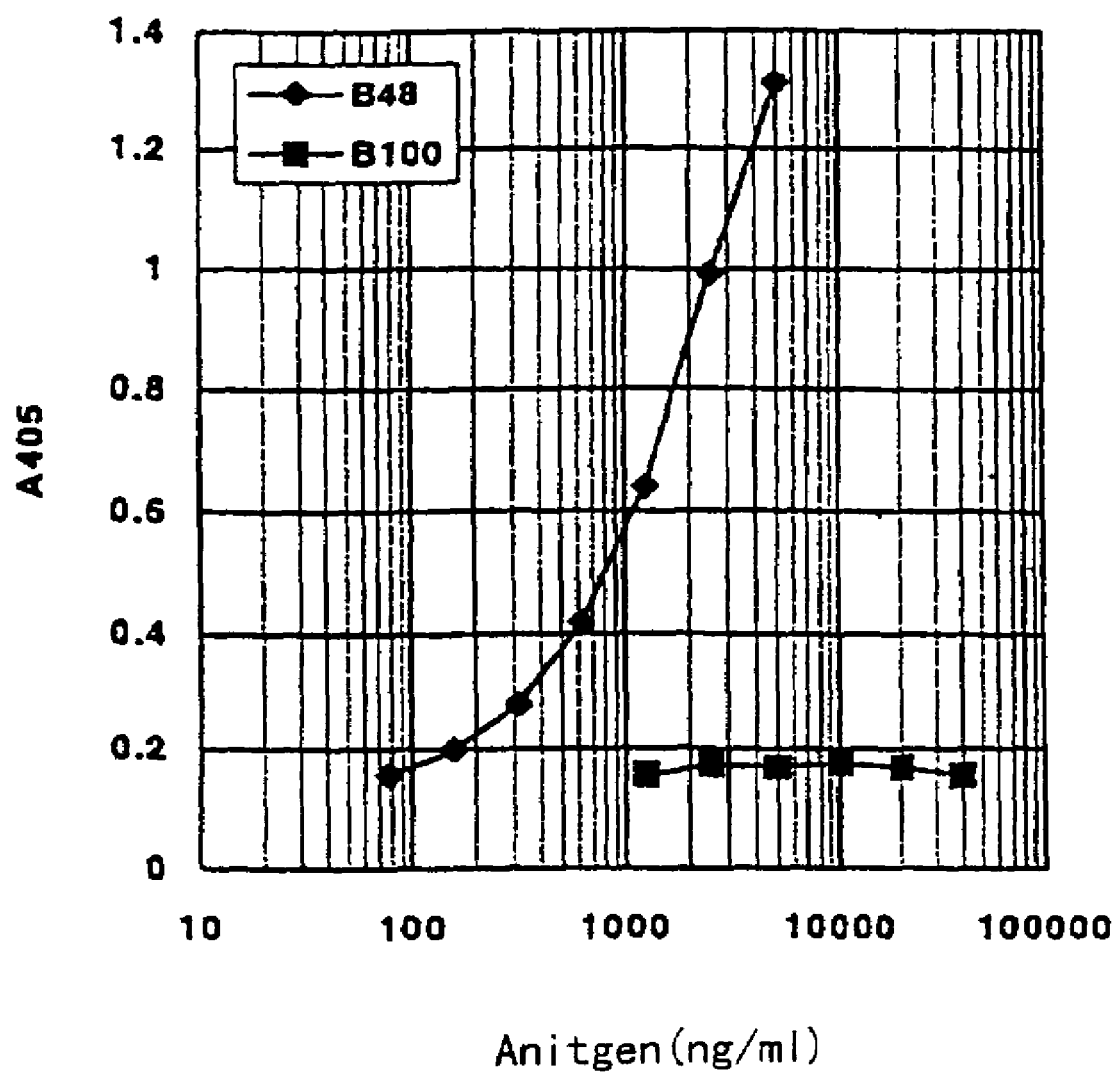
FIG. 3 shows the calibration curves obtained in ELISA utilizing immobilized monoclonal antibody B48-151, obtained in Example 6.

The results are shown in FIG. 3. As shown in FIG. 3, apo-B-48 can be measured by ELISA using immobilized monoclonal antibody B48-151 and apo-B-100 was not measured by this ELISA.

Example 7

Measurement of Apo-B-48 in Sera by ELISA Using Immobilized Monoclonal Antibody B48-151

Apo-B-48 was measured in the same manner as in Example 6 except that the samples were sera 20-fold diluted with 1% BSA-PBS (pH7.4). The sample sera were pooled frozen sera from 8 healthy individuals (Sample Nos. 1–8), collected when fasted or 1 hour after eating. The results are shown in FIG. 4.

Figure 4:
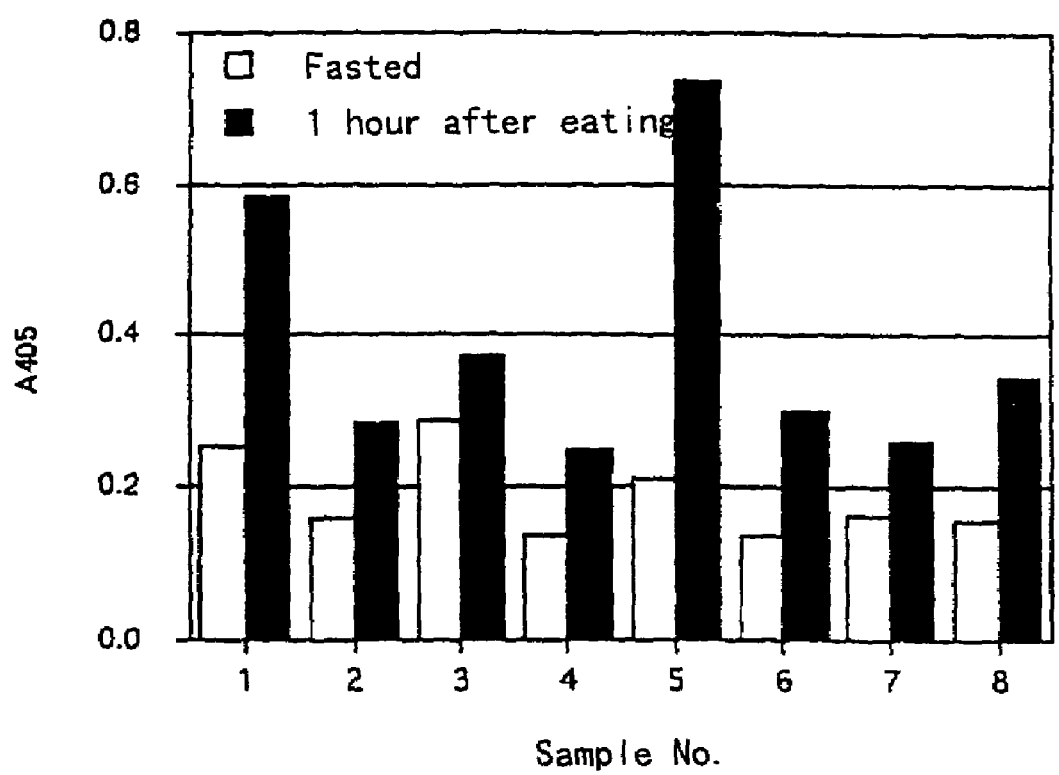
FIG. 4 shows the results of the ELISA utilizing immobilized monoclonal antibody B48-151, which was carried out using sera from healthy individuals as samples, obtained in Example 7.

As shown in FIG. 4, in all samples, the measured apo-B-48 values were higher at 1 hour after eating than those during fasting. This is in agreement with the behavior of CM.

Example 8

Treatment of Sera with Surfactants

The reaction in the ELISA using the immobilized monoclonal antibody B48-151 in case of adding various surfactants to the reaction mixture when the immobilized antibody and the sera were reacted was studied. The surfactants used were anionic surfactants which were SDS (purchased from Nacalai Tesque) and sodium deoxycholate (purchased from Wako Pure Chemicals), and nonionic surfactants which were Triton X-100 (purchased from Nacalai Tesque), Triton X-114 (purchased from Nacalai Tesque), Tween-20 (purchased from Nacalai Tesque), Tween-80 (purchased from Nacalai Tesque), NP-40 (purchased from Sigma), MEGA-8 (purchased from Dojindo Laboratories) and Brij-35 (purchased from Sigma).

Figure 5:
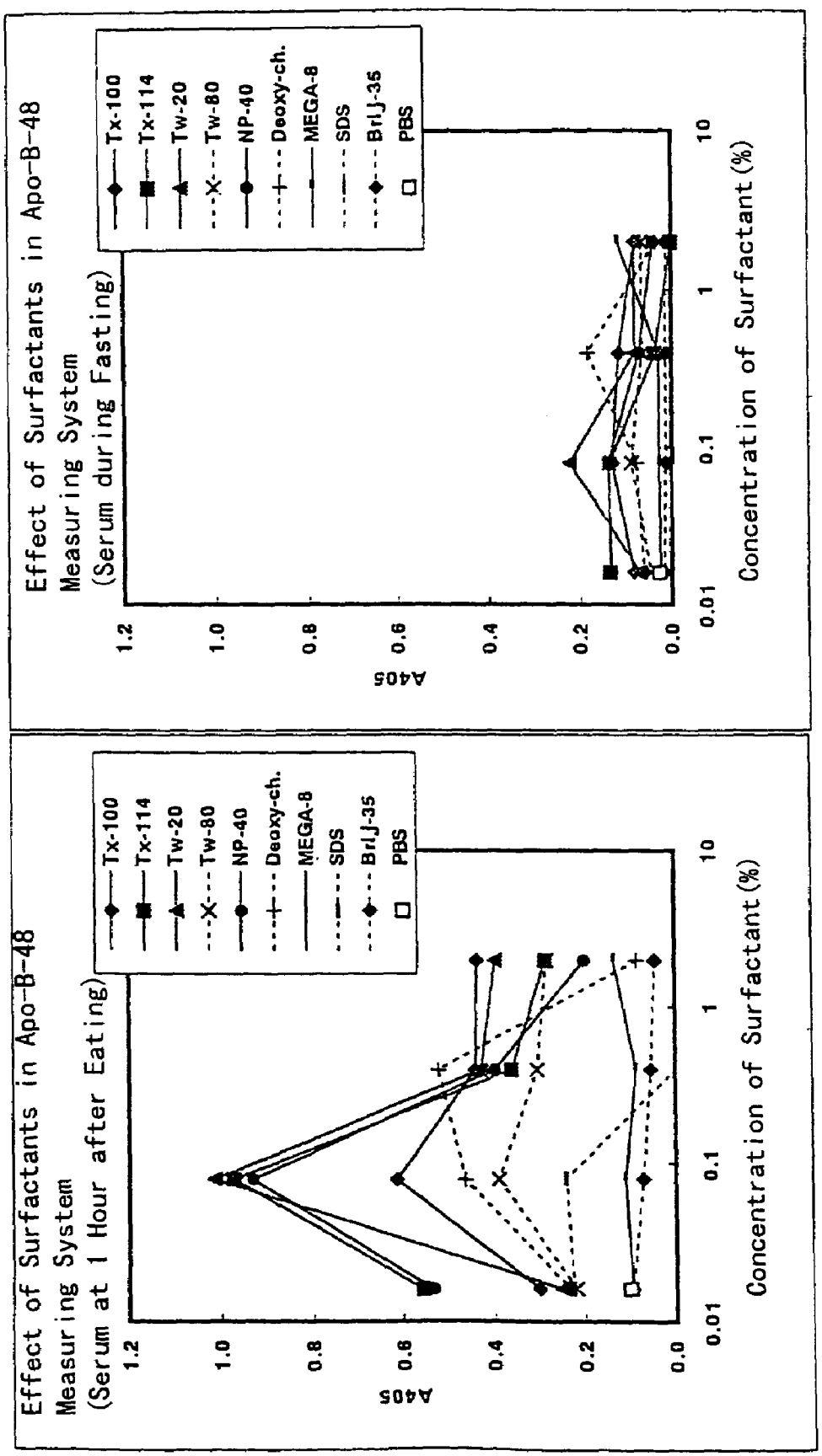
FIG. 5 shows the results of the ELISA utilizing immobilized monoclonal antibody B48-151, which was carried out in the presence or absence of various surfactants, which results were obtained in Example 8.

Monoclonal antibody B48-151 dissolved in PBS (pH7.4) at a concentration of 10 µg/ml was placed in wells of an ELISA plate (Maxisorb, commercially available from Nunc) in an amount of 75 µl/well, and the plate was left to stand at 4° C. overnight, thereby adsorbing the antibody to the wells. Then 1% BSA-PBS (pH7.4) was added to the wells in an amount of 150 µl/well and the plate was incubated at 37° C. for 5 hours, thereby carrying out masking. After washing the plate three times with the washing buffer, sera 20-fold diluted with PBS (pH7.4) containing one of the surfactants at a concentration of 2%, 0.4%, 0.08% or 0.016% by weight were placed to the wells in an amount of 75 µl/well, and reaction was allowed to occur at 37° C. for 1 hour. After washing the plate three times with the washing buffer, anti-human apo-B-100 monoclonal antibody (B100-228) labeled with alkaline phosphatase prepared by the method of Yoshitake et al. dissolved in PBS (pH7.4) was added to the wells in an amount of 75 µl/well, and reaction was allowed to occur at 37° C. for 1 hour. The plate was then sufficiently washed with the washing buffer and the substrate 4-nitrophenol phosphate was added to the wells in an amount of 75 µl/well. After incubating the plate at 37° C. for 30 minutes, absorbance at 405 nm was measured. As the samples, fresh sera from healthy individuals collected at 1 hour after eating and fresh sera from healthy individuals collected when fasted were used. The results are shown in FIG. 5. In FIG. 5, "Tx-100" indicates Triton X-100, "Tx-114" indicates Triton X-114, "Tw-20" indicates Tween 20, "Tw-80" indicates Tween 80, "Deoxy-ch." indicates sodium deoxycholate, and PBS indicates PBS containing no surfactants.

As shown in FIG. 5, in cases where the serum was diluted with PBS (pH7.4) which did not contain any surfactant, coloring was not observed at all, so that it was judged that the C-terminal epitope of apo-B-48 was not exposed. In cases where the PBS (pH 7.4) containing a surfactant was used, strong coloring was observed when a nonionic surfactant such as Triton X-100, Tween 20 or NP-40 at a concentration of about 0.1% was used. Thus, it was judged that the C-terminal epitope of apo-B-48 was exposed by the treatments with these surfactants. On the other hand, in cases where MEGA-8, Brij-35 or SDS was used, the coloring was week or almost no coloring was observed. Taking the results of Example 9 described below into consideration, it was judged that MEGA-8 has poor ability to expose the C-terminal epitope of apo-B-48; that SDS, especially at a concentration of not less than 0.1% inhibits the immunological reaction; and that Brij-35 has a poor ability to expose the C-terminal epitope of apo-B-48 and inhibits the immunological reaction.

Example 9

Influence by Surfactants on Immunological Reaction

The reaction between immobilized peptide C6 and the monoclonal antibody B48-151 when the same surfactants as in Example 8 were added to the reaction mixture was studied. Peptide C6 dissolved in PBS (pH7.4) at a concentration of 1 µg/ml was placed in wells of an ELISA plate (Maxisorb, commercially available from Nunc) in an amount of 75 µl/well, and the plate was left to stand at 4° C. overnight, thereby adsorbing the peptide C6 to the wells. Then 1% BSA-PBS (pH7.4) was added to the wells in an amount of 150 µl/well and the plate was incubated at 37° C. for 5 hours, thereby carrying out masking. After washing the plate three times with the washing buffer, monoclonal antibody B48-151 dissolved in PBS (pH7.4) to a concentration of 2.5 µg/ml, which PBS contained one of the surfactants at a concentration of 2%, 0.4%, 0.08% or 0.016% by weight were placed to the wells in an amount of 75 µl/well, and reaction was allowed to occur at 37° C. for 1 hour. After washing the plate three times with the washing buffer, POD-labeled mouse immunoglobulin antibody (purchased form Daco) was added to the wells in an amount of 75 µl/well, and reaction was allowed to occur at 37° C. for 1 hour. The plate was then sufficiently washed with the washing buffer and the substrate ABTS was added to the wells in an amount of 75 µl/well. After incubating the plate at 37° C. for 15 minutes, absorbance at 405 nm was measured. The results are shown in FIG. 6.

Figure 6:
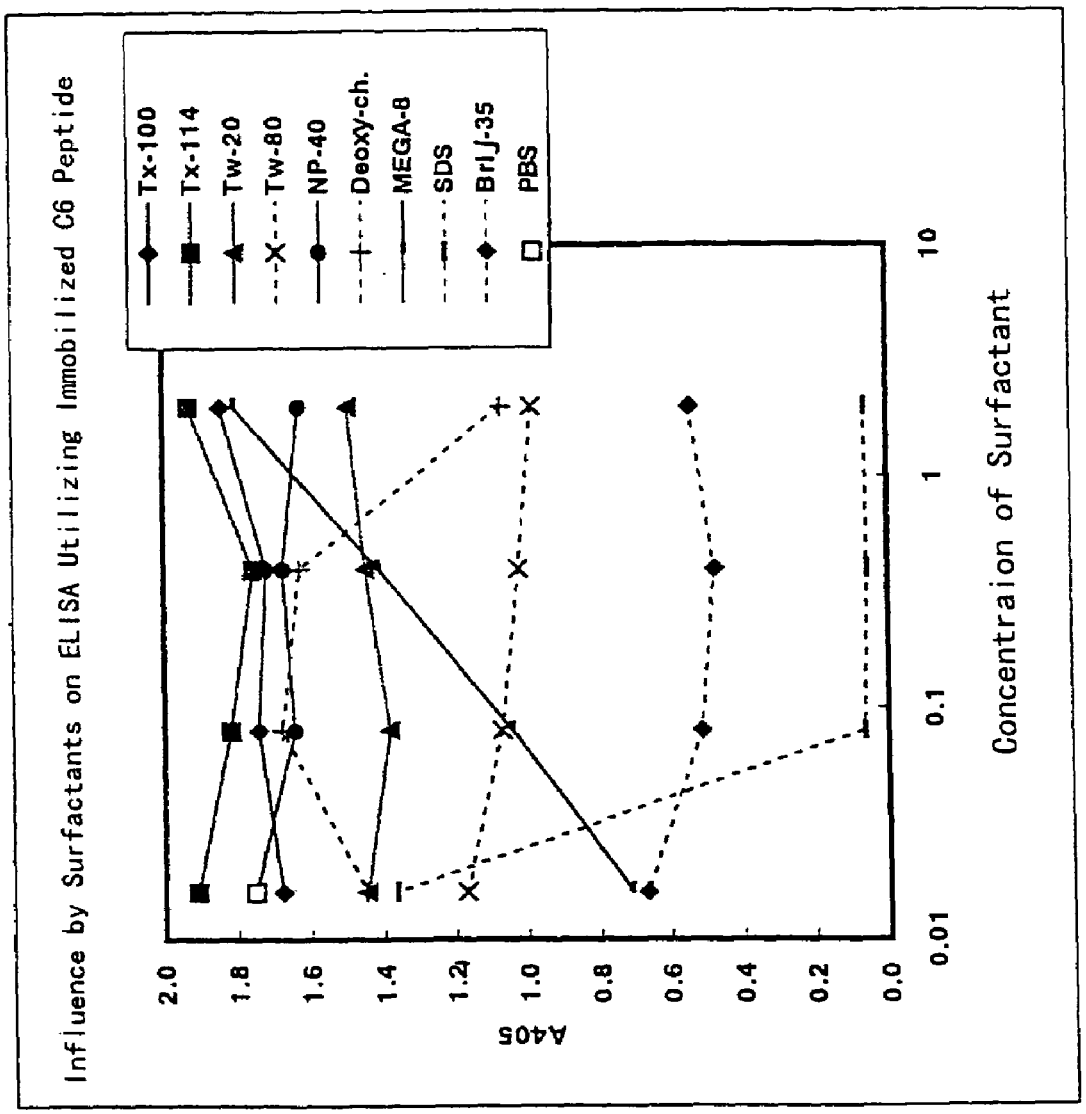
FIG. 6 shows the results of the ELISA utilizing immobilized peptide C6, in the presence or absence of various surfactants, which results were obtained in Example 9.

As shown in FIG. 6, influence by a nonionic surfactant such as Triton X-100, Tween 20 or NP-40 on the immunological reaction was not observed at all. On the other hand, influence by Brij-35 or SDS on the immunological reaction was observed. Especially, SDS completely inhibited the immunological reaction at a concentration of not less than 0.1% by weight.

We claim:

1. A method for measuring apo-B-48 in a test sample, comprising:
   a) incubating the test sample with a monoclonal antibody that specifically bind to apo-B-48 and which does not bind to apo-B-100;
   b) allowing a complex between apo-B-48 and the antibody to form;
   c) adding a labeled second antibody capable of binding to apo-B-48;
   d) detecting resultant labeled complexes; and
   e) correlating the detected complex with the presence of apo-B-48 in the test sample;
   wherein apo-B-48 in said test sample is subjected to a treatment with one or more nonionic surfactants by which the corresponding epitope of said monoclonal antibody is exposed before or simultaneously with an antigen-antibody reaction.

2. The method according to claim 1, wherein said monoclonal antibody is immobilized on a solid carrier, and apo-B-48 immobilized on said carrier through said monoclonal antibody is measured after said antigen-antibody reaction.

3. The method according to claim 2, which is carried out by ELISA.

* * * * *